United States Patent
Nalewajek et al.

(10) Patent No.: US 10,021,879 B2
(45) Date of Patent: Jul. 17, 2018

(54) FUMIGANT COMPOSITIONS AND METHODS BASED ON HEXAFLUOROPROPYLENE OXIDE (HFPO)

(71) Applicant: Honeywell International Inc., Morris Plains, NJ (US)

(72) Inventors: David Nalewajek, West Seneca, NY (US); Andrew J. Poss, Kenmore, NY (US); Cheryl L. Cantlon, Clarence Center, NY (US)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 15/708,381

(22) Filed: Sep. 19, 2017

(65) Prior Publication Data

US 2018/0077932 A1 Mar. 22, 2018

Related U.S. Application Data

(60) Provisional application No. 62/397,690, filed on Sep. 21, 2016.

(51) Int. Cl.
| | |
|---|---|
| *A01N 43/20* | (2006.01) |
| *A01N 43/24* | (2006.01) |
| *A61K 31/335* | (2006.01) |
| *A01N 25/30* | (2006.01) |
| *A01N 29/02* | (2006.01) |

(52) U.S. Cl.
CPC ............. *A01N 43/20* (2013.01); *A01N 25/30* (2013.01); *A01N 29/02* (2013.01)

(58) Field of Classification Search
None
See application file for complete search history.

(56) References Cited

U.S. PATENT DOCUMENTS

| | | | |
|---|---|---|---|
| 1,051,647 A | 1/1913 | Taylor | |
| 3,573,330 A | 3/1971 | Dear et al. | |
| 9,232,788 B2 | 1/2016 | Poss et al. | |
| 2013/0109570 A1* | 5/2013 | Poss | A01N 29/02 504/140 |
| 2015/0024019 A1 | 1/2015 | Ali et al. | |

FOREIGN PATENT DOCUMENTS

| | | | |
|---|---|---|---|
| CN | 103931404 A | * | 7/2014 |
| GB | 1051647 A | | 12/1996 |
| RU | 2196771 C1 | | 1/2003 |

OTHER PUBLICATIONS

Oberg, Tomas: "A QSAR for the Hydroxyl Radical Reaction Rate Constant: Validation, Domain of Application, and Prediction." Atmospheric Environment, 39:2189-2200, 2005.

* cited by examiner

*Primary Examiner* — Jared D Barsky
(74) *Attorney, Agent, or Firm* — Faegre Baker Daniels LLP

(57) ABSTRACT

Fumigant compositions including hexafluoropropylene oxide (HFPO) and methods of preparing such compositions are provided. The fumigant compositions may be suitable for use as soil fumigant compositions and structural fumigant compositions against a variety of undesirable species such as weeds, nematodes, pathogens, animals and insects. The fumigant compositions also have low toxicity and low Global Warming Potential (GWP).

20 Claims, 1 Drawing Sheet

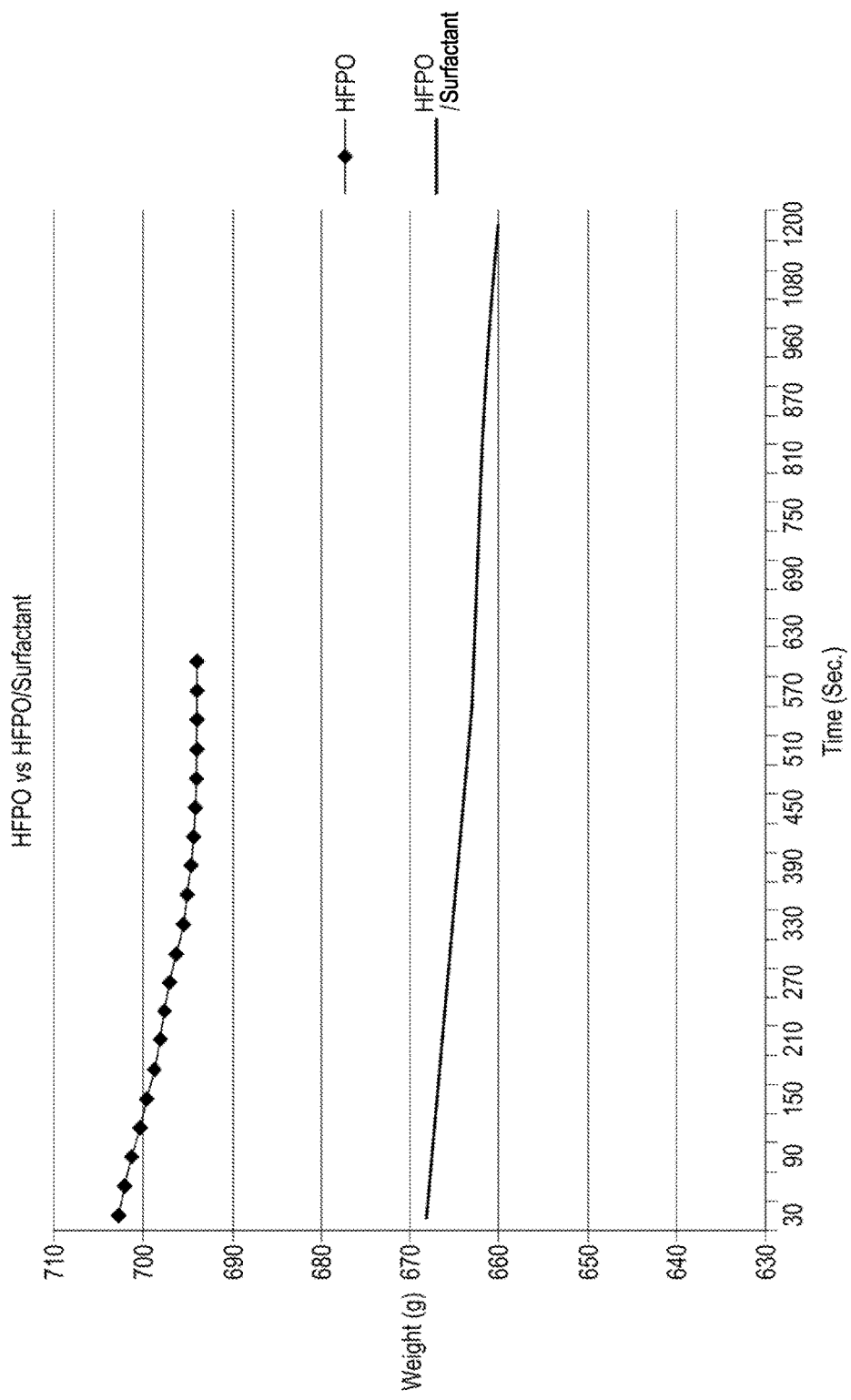

FUMIGANT COMPOSITIONS AND METHODS BASED ON HEXAFLUOROPROPYLENE OXIDE (HFPO)

CROSS REFERENCE TO RELATED APPLICATIONS

This application claims the benefit under Title 35, U.S.C. § 119(e) of U.S. Provisional Patent Application Ser. No. 62/397,690, entitled FUMIGANT COMPOSITIONS AND METHODS BASED ON HEXAFLUOROPROPYLENE OXIDE (HFPO), filed on Sep. 21, 2016, the entire disclosure of which is expressly incorporated by reference herein.

FIELD OF THE INVENTION

The present disclosure relates to compositions and formulations for soil and structural fumigation, methods of preparing such formulations, and methods of fumigating soil and structures with such compositions.

DESCRIPTION OF RELATED ART

Historically, methyl bromide ($CH_3Br$) has been the most widely used and most universal fumigant in the world. It is known for being extremely effective as a herbicide, nematocide, insecticide and fungicide. Consequently, it has been used extensively for soil fumigation, as a commodity quarantine treatment for exports and imports, to control a variety of pests on numerous crops, and as a structural fumigant applied to building surfaces. However, methyl bromide contributes to the depletion of the ozone layer in the stratosphere. In accord with the Montreal Protocol, the import and manufacture of methyl bromide in the United States and other developed countries was banned in 2005.

Various compounds such as 1,3-dichloropropene, chloropicrin, metam sodium, and methyl iodide have been identified as alternatives to methyl bromide. These alternatives are commonly applied as mixtures of two or more of the individual compounds in order to attempt to produce a broader spectrum product similar to methyl bromide.

The global warming potential (GWP) of new fumigants is scrutinized. GWP is a relative measure of how much heat a greenhouse gas traps in the atmosphere, and is a comparison of the amount of heat trapped by a certain mass of the gas in question to the amount of heat trapped by a similar mass of carbon dioxide. GWP is calculated over a specific time interval, commonly 20, 100 or 500 years. GWP is expressed as a factor of carbon dioxide (whose GWP is standardized to 1). For example, the 20 year GWP of methane is 56, which means if the same weights of methane and carbon dioxide were introduced into the atmosphere, that methane will trap 56 times more heat than the carbon dioxide over the next 20 years.

New fumigants which are effective yet environmentally benign are desired.

SUMMARY OF THE INVENTION

Fumigant compositions and methods of preparing such compositions are provided. The fumigant compositions may be suitable for use as soil fumigant compositions and/or structural fumigant compositions.

In one form thereof, the present invention provides a method of eradicating undesirable species from a treatment zone including the step of contacting the treatment zone with a fumigant composition including hexafluoropropene oxide (HFPO). In any of the present embodiments, the undesirable species may include one or more of weeds, nematodes or pathogens and/or may include insects or animals. In any of the present embodiments, the treatment zone may be, for example, a building, a vehicle, packaged goods, or a field. The fumigant may be applied to soil via drip irrigation or shank injection.

In any of the present embodiments, the fumigant composition may be in gaseous or aqueous form, and may further include an additional additive ingredient of at least one of methyl iodide, chloropicrin, acrolein, 1,3-dichloropropene, dimethyl disulfide, furfural, propylene oxide or metam sodium. In any of the present embodiments, the fumigant composition may further include at least one surfactant and/or at least one odorant.

In another form thereof, the present invention provides a fumigant composition, including hexafluoropropylene oxide (HFPO), at least one component selected from methyl iodide, chloropicrin, acrolein, 1,3-dichloropropene, dimethyl disulfide, furfural, propylene oxide metam sodium and combinations, and at least one surfactant.

In any of the present embodiments, the additional additive component may be methyl iodide, or any of those listed above, and in one particular embodiment, the composition may include hexafluoropropropylene oxide, methyl iodide, and at least one surfactant. In any of the present embodiments, the surfactant, if present, may be a nonionic surfactant and may be a polysorbate.

In a further form thereof, the present invention provides a method of making a fumigant composition including the step of combining methyl iodide, a surfactant, and at least one of hexafluoropropylene oxide (HFPO) in water.

BRIEF DESCRIPTION OF THE DRAWINGS

The above mentioned and other features of the invention, and the manner of attaining them, will become more apparent and the invention itself will be better understood by reference to the following description of embodiments of the invention taken in conjunction with the accompanying drawings.

FIG. 1 corresponds to Example 2, and illustrates solubility data for HFPO vs. HFPO with surfactant.

Corresponding reference characters indicate corresponding parts throughout the several views. Although the drawings represent embodiments of various features and components according to the present disclosure, the drawings are not necessarily to scale and certain features may be exaggerated in order to better illustrate and explain the present disclosure. The exemplification set out herein illustrates an embodiment of the invention, and such exemplification is not to be construed as limiting the scope of the invention in any manner.

DETAILED DESCRIPTION

Embodiments of the present invention include fumigant compositions including a perfluorinated epoxy propane, specifically 1,2-hexafluoropropylene oxide (HFPO), which has a low toxicity and a low atmospheric lifetime, specifically, less than 10 years, such as 5 years or less, or even 1 year or less.

The present fumigant compositions may be used against a variety of different undesirable species, such as weeds, nematodes or pathogens. In some embodiments, the fumigant compositions may be used against a variety of different insects, including but not limited to termites, cockroaches, mites and bed bugs, as well as animals such as gophers, mice, moles, rats and other rodent pests.

The present fumigant compositions may be used in a variety of different treatment zones. As uses herein, a "treatment zone" is a surface, space or volume that contains undesirable species. In some embodiments, for example, the treatment zone may be a building, such as a warehouse or commercial space, or a vehicle, such as a tractor trailer or a rail car.

I. Fumigant Composition.

The present fumigant composition comprises, consists essentially of, or consists of, 1,2-hexafluoropropylene oxide or hexafluoropropylene oxide (HFPO), which has the following chemical structure:

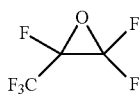

HFPO may be present in an initial mixture (e.g., prior to diluting into a use solution) in an amount as low as about 1 weight percent (wt. %), in an amount as low as about 30 wt. %, in an amount as low as about 40 wt. %, or in an amount as low as about 50 wt. %. The HFPO may be present in an initial mixture, prior to dilution, in an amount as high as about 75 wt. %, in an amount as high as about 85 wt. %, in an amount as high as about 95 wt. %, or in an amount as high as about 99 wt. %. HFPO may further be present within any range delimited by any pair of the foregoing values set forth in this paragraph.

In addition to the HFPO, the present fumigant compositions may also include at least one additional active ingredient. Suitable additional active ingredients for the fumigant compositions include, but are not limited to, methyl iodide, chloropicrin, acrolein, 1,3-dichloropropene, dimethyl disulfide, furfural, metam sodium and propylene oxide. In certain embodiments, the HFPO may be used with or without additional active ingredients.

Each additional active ingredient, such as methyl iodide, can be present in the initial mixture in any suitable amount, including for example, in an amount as low as about 0.5 wt. %, in an amount as low as about 5 wt. %, in an amount as low as about 15 wt. % or in an amount as low as about 25 wt. %. Each additional active ingredient, such as methyl iodide, can be present in the initial mixture in an amount as high as about 50 wt. %, in an amount as high as about 60 wt. % or in an amount as high as about 70 wt. %. Each additional active ingredient, such as methyl iodide, may further be present within any range delimited by any pair of the foregoing values set forth in this paragraph.

The fumigant compositions according to embodiments of the present invention may further include various additives. In one embodiment, the fumigant composition may include at least one surfactant. Suitable surfactants for use in fumigant compositions can be ionic surfactants or non-ionic surfactants. Non-ionic surfactants that can be suitable in fumigant compositions include, but are not limited to: Arkopal™ (a nonylphenol ethoxylate), Cetomacrogol™ 1000 (a polyethylene glycol), cetostearyl alcohol, cetyl alcohol, cocamide DEA, cocamide MEA, decyl glucoside, glyceryl laurate, lauryl glucoside, narrow range ethoxylates, nonoxynols, NP-40, octaethylene glycol monododecyl ether, octyl glucoside, oleyl alcohol, pentaethylene glycol, monododecyl ether, poloxamer, polyglycerol polyricinoleate, polysorbate, polysorbate 20, polysorbate 40, polysorbate 60, polysorbate 80, sorbitan monostearate, sorbitan tristearate, stearyl alcohol, Triton™ X-100 (polyethylene oxide chain with an aromatic hydrocarbon group), and Tween™ 80 (a polysorbate). In one specific example, the surfactant can be a polysorbate, which can be polysorbate 20, polysorbate 40, polysorbate 60 or polysorbate 80.

The amount of surfactant used can be in an amount as low as 0.1 wt. %, in an amount as low as 3 wt. % or in an amount as low as 5 wt. %. The surfactant can be included in an amount that is as high as 15 wt. %, in an amount as high as 30 wt. %, or in an amount as high as 50 wt. %. The surfactant may further be present within any range delimited by any pair of the foregoing values set forth in this paragraph, such as between 0.1 wt. % and 30 wt. %, or between 5 wt. % to 15 wt. %, for example.

In some embodiments, the HFPO can be diluted with a suitable carrier solvent that can include at least one C3-C4 hydrofluorocarbon olefin or at least one hydrochlorofluorocarbon olefin which preferably have a combination of desirable environmental and functional properties. For example, environmentally, the carrier solvents can have an ozone depletion potential (ODP) that is zero or about zero. Carrier solvents may also have a low global warming potential, which can preferably be less than or equal to about 10 relative to $CO_2$. Functionally, carrier solvents are preferably volatile, non-toxic, and non-flammable. Co-solvents for use with this technology include mixtures of tetrafluoropropenes, hexafluorobutenes and chlorotrifluoropropenes. The carrier solvents can include an azeotropic or azeotrope-like mixture of the at least one C3-C4 hydrofluorocarbon olefin or the at least one hydrochlorofluorocarbon olefin with an organic compound.

The amount of solvent used can be in an amount as low as 1 wt. % and in an amount that is as high as 5 wt. %, in an amount as high as 50 wt. %, or in an amount as high as 99 wt. %. The solvent may further be present within any range delimited by any pair of the foregoing values set forth in this paragraph, such as between 1 wt. % and 99 wt. %, or between 1 wt. % to 50 wt. %, or between 1 wt. % and 5 wt., for example.

For safety purposes, the fumigant composition may include an odorant such as banana oil or chloropicrin since HFPO has no detectable odor.

II. Application Techniques.

The fumigant composition may be applied to soil or structures as part of an aqueous solution or dispersion. The fumigant composition may by applied by a number of different procedures that are currently employed for soil and structural treatments.

In some embodiments, soil fumigant may utilize either shank injection or drip irrigation. In shank injection fumigant, the chemical fumigant is applied to the soil by injection through hollow shanks that are pulled through the soil, either at shallow depths followed by plastic mulch film application, or at deep depths followed by soil compaction.

Application of the chemical fumigant via drip irrigation involves introducing and dispersing the chemical fumigant through an existing irrigation system. This provides an advantage of minimizing potential exposure to workers, as this can be done without workers in the field.

The irrigation system may include one or more dripperlines having a plurality of emitters therein. The emitters, also known as drippers, can be of any suitable type, including for example pre-punched holes or porous pipe. The emitters can be formed as an integral part of a dripperline, or can be separately produced and installed on or in the one or more dripperlines. The emitters can be spaced apart at any suitable distance, including for example, from about 8 inches apart to about 24 inches apart (from 200 mm to 600 mm apart).

In some examples, the one or more dripperlines can be placed below the soil that is to be fumigated. Application of the fumigant composition to the soil can include providing pressure to cause the fumigant composition to flow through the one or more dripperlines and exit the one or more dripperlines through the plurality of emitters to contact and flow into the soil. Alternatively, the fumigants may be applied to the soil by tractor mounted injectors, manually in canisters or as a gas through lay-flat tubing.

The behavior of the fumigant compositions in use is a function of their water solubility, volatility, hydrolysis and degradation rates, and their sorption to soil organic matter and clay. The physical and chemical properties of the fumigants, such as water solubility, vapor pressure, boiling point, Henry's constant and half-life in soil, are good indicators of how each chemical will behave in the soil-air-water system. The efficacy of a fumigant correlates to its distribution patterns in soils and applications that maximize concentrations in the pest-infested zone to provide better control.

For structural fumigation the chemicals may be heated to a gas before introduction within a building, chamber, vehicle or other space or structure. The space or structure is preferably sealed with a tarpaulin, fumigant tape or gas impermeable sheeting. In some embodiments, structural fumigant, particularly for rodents, involves sealing the structure as tightly as possible. In some embodiments, a 2 to 4 mil polyethylene cover may be used to wrap the structure before providing the fumigant composition. In some embodiments, the structure may subsequently be aerated to remove the fumigant composition.

Stacked commodities may be treated by draping the commodities with a gas-impermeable tarp or sheet that can be sealed to an impermeable surface (such as a concrete floor) using, for example, sand-filled tubes. After sufficient fumigant composition has been released under the tarp, the space may be aerated to remove any remaining fumigant composition.

The fumigant compositions can be prepared by combining HFPO, the optional active, at least one surfactant and water to form a fumigant composition. The fumigant composition can be a solution or a homogeneous mixture, which can be formed by mixing the combined initial mixture, the at least one surfactant and the water under suitable conditions. In one example, the fumigant compositions can be formed by mixing the components at a temperature at or below about 60° F. (15.5° C.).

EXAMPLE 1

Fumigant tests on seeds of the broadleaf species *Abutilon theophrasti* Medik and the grass weed species *Lolium multiflorum* Lam demonstrate that HFPO completely prevented seed germination. Since weeds are generally more resistant to fumigant than most nematodes or soil-borne plant-pathogenic fungi (See Ohr et al., "Methyl Iodide, an Ozone-Safe Alternative to Methyl Bromide and a Soil Fumigant," Plant Disease, July 1996, pp. 731-735; See also Zhang et al., "Effect of Soil Physical Factors on Methyl Iodide and Methyl Bromide", Pestic. Sci. 1998, pp. 53, 71-79), this result indicates that HFPO can be employed as a fumigant for the effective control of plant pathogens, nematodes, bacteria and weeds.

In particular, in 440 mL pressure vessels, fourteen seeds of *Abutilon theophrasti* Medik and fifteen seeds of *Lolium multiflorum* Lam were thoroughly mixed with 50 mL (approximately 30 grams) of soil and 6 ml of water. The filled vessels were kept at room temperature for 20-24 hours to allow the seeds to imbibe water before treatment. The vessels were sealed and evacuated, and then 80 ml, 160 ml and 440 ml, respectively, of gaseous HFPO was added. The vessels were thoroughly mixed and placed horizontally on the laboratory bench at ambient temperature for two days. The contents of each bottle were transferred to a plastic sterile Petri dish containing 7 mL of water. The Petri dishes were sealed with parafilm and incubated in the laboratory at ambient temperature. After 10 days, the number of germinated seeds was counted. As shown in Table 1 below, none of the seeds treated with HFPO showed any signs of germination.

TABLE 1

Seeds germinated based on species

| Fumigant | Abutilon theophrastic Medik (seeds germinated) | Loliium multiflorum Lam (seeds germinated) |
|---|---|---|
| Control | 14 | 15 |
| 80 ml HFPO | 0 | 0 |
| 160 ml HFPO | 0 | 0 |
| 440 ml HFPO | 0 | 0 |

EXAMPLE 2

Experimentation was carried out to determine the volatility of aqueous fumigant compositions, both with and without inclusion of a surfactant. In each case, HFPO was placed in a chilled 500 ml Fischer Porter tube that was equipped with a vent to remove any gases. The vessel was cooled to 0° C. and was charged with varying amounts of water, HFPO and surfactant. The temperature was equilibrated to 20° C. and the reactor was placed on a balance. The vent tube was opened and the weight loss was recorded every 30 seconds.

In analyzing the effects of adding surfactant to an aqueous solution of HFPO, 10.0 grams of HFPO was added to 40 grams of water. In a separate experiment, 10 grams of HFPO and 4.0 grams of Tween™ 80 were added to 40.0 grams of water. FIG. 1 provides a graphical representation of the numerical data comparing the volatility of an aqueous solution of HFPO, both with and without inclusion of the Tween™ 80 nonionic surfactant. As can be seen, inclusion of the surfactant provides for longer retention of the HFPO in solution.

The invention claimed is:
1. A method of eradicating undesirable species from a field, the method comprising:
    contacting the field with a fumigant composition comprising hexafluoropropene oxide (HFPO).
2. The method of claim 1, wherein the contacting step comprises contacting soil with the fumigant composition.
3. The method of claim 2, wherein contacting soil comprises contacting soil via drip irrigation.
4. The method of claim 2, wherein contacting soil comprises contacting soil via shank injection.
5. The method of claim 1, wherein the fumigant composition is in gaseous form.
6. The method of claim 1, wherein the fumigant composition is in aqueous form.
7. The method of claim 1, wherein the fumigant composition further comprises at least one of methyl iodide, chloropicrin, acrolein, 1,3-dichloropropene, dimethyl disulfide, furfural, propylene oxide or metam sodium.

8. The method of claim 1, wherein the fumigant composition further comprises at least one surfactant.

9. The method of claim 1, wherein the fumigant composition comprises at least one odorant.

10. The method of claim 1, wherein the fumigant composition comprises between 75 wt. % and 99 wt. % hexafluoropropene oxide (HFPO), based on a total weight of the fumigant composition.

11. The method of claim 1, wherein the fumigant composition comprises between 85 wt. % and 95 wt. % hexafluoropropene oxide (HFPO), based on a total weight of the fumigant composition.

12. The method of claim 1, wherein the fumigant composition comprises between 1 wt. % and 50 wt. % hexafluoropropene oxide (HFPO), based on a total weight of the fumigant composition.

13. The method of claim 1, wherein the fumigant composition comprises between 1 wt. % and 30 wt. % hexafluoropropene oxide (HFPO), based on a total weight of the fumigant composition.

14. The method of claim 8, wherein the fumigant composition comprises between 0.1 wt. % and 5 wt. % of the at least one surfactant, based on a total weight of the fumigant composition.

15. The method of claim 8, wherein the fumigant composition comprises between 15 wt. % and 50 wt. % of the at least one surfactant, based on a total weight of the fumigant composition.

16. The method of claim 6, wherein the fumigant composition further comprises at least one solvent.

17. The method of claim 16, wherein the at least one solvent is present in an amount between 1 wt. % and 5 wt. %, based on a total weight of the fumigant composition.

18. The method of claim 16, wherein the at least one solvent is present in an amount between 5 wt. % and 50 wt. %, based on a total weight of the fumigant composition.

19. The method of claim 1, wherein the fumigant composition further comprises methyl iodide present in an amount between 5 wt. % and 25 wt. %, based on a total weight of the fumigant composition.

20. The method of claim 1, wherein the fumigant composition further comprises methyl iodide present in an amount between 50 wt. % and 70 wt. %, based on a total weight of the fumigant composition.

* * * * *